United States Patent [19]
Torgerson et al.

[11] Patent Number: 5,820,589
[45] Date of Patent: Oct. 13, 1998

[54] IMPLANTABLE NON-INVASIVE RATE-ADJUSTABLE PUMP

[75] Inventors: Nathan A. Torgerson, White Bear Lake; Raymond F. McMullen, Shorewood, both of Minn.

[73] Assignee: Medtronic, Inc., Minneapolis, Minn.

[21] Appl. No.: 641,363

[22] Filed: Apr. 30, 1996

[51] Int. Cl.⁶ .................................................. A61M 11/00
[52] U.S. Cl. ............................................................ 604/93
[58] Field of Search ........................... 604/891.1, 65–67, 604/93, 131, 152, 246–249, 890.1; 128/DIG. 12, DIG. 13

[56] References Cited

U.S. PATENT DOCUMENTS

| | | | |
|---|---|---|---|
| 4,714,462 | 12/1987 | DiDomenico | 604/67 |
| 4,931,050 | 6/1990 | Idriss | 604/891.1 |
| 5,061,242 | 10/1991 | Sampson | 604/246 |
| 5,207,666 | 5/1993 | Idriss et al. | 604/891.1 |

FOREIGN PATENT DOCUMENTS 0 300 552 A1  12/1988  European Pat. Off. ......... A61M 5/14
0 647 453 A1  4/1995  European Pat. Off. .

OTHER PUBLICATIONS

Notification of Transmittal of the International Search Report mailed Sep. 10, 1997 for International Application No. PCT/US 97/07114.

International Search Report for International Application No. PCT/US 97/07114.

*Primary Examiner*—Manuel Mendez
*Attorney, Agent, or Firm*—Arnold, White & Durkee

[57] ABSTRACT

In accordance with the present invention, an implantable pump is programmed non-invasively by means of a programmer that communicates flow rate information by means of radio frequency telemetry or other methods of non-invasive telemetry. The programmer also supplies power to the implantable pump during programming. The implanted rate-adjustable pump that receives rate information and power by telemetry preferably does not include a battery or any other type of internal power supply, relying only on the energy obtained from the programmer through telemetry.

8 Claims, 3 Drawing Sheets

IMPLANTABLE NON-INVASIVE RATE-ADJUSTABLE PUMP

FIELD OF THE INVENTION

The present invention relates generally to a method and apparatus for the delivery of fluid to a specific desired location within a patient's body; and, more particularly, relates to an implantable non-invasive, rate-adjustable pump for the delivery of pharmaceutical agents or other fluids to an implanted catheter or a desired location in a patient's body.

BACKGROUND OF THE INVENTION

Pharmaceutical agents and other fluids increasingly are being administered to patients through the use of pumps implanted within the patients' bodies. Generally, these drug infusion pumps may be classified as either fixed- or variable-rate pumps, depending upon the pump's flow rate characteristics.

Fixed rate implantable pumps typically are manufactured to deliver fluid at a preset flow rate. After manufacturing, the flow rate can not be changed. If a different rate is required by the patient, the original pump would need to be removed and a pump manufactured at the new flow rate would need to be implanted. An example of one such pump in use today is the Model 400™ manufactured by Infusaid.

Variable flow rate implantable pumps typically require that, prior to implantation, some mechanical means, e.g., a screwdriver be used by physicians to set the rate at which the fluids will be delivered to the patient. After implantation, these pumps cannot be reset to a new flow rate without the pump being removed from the patient's body. An example of one such pump in use today is the IP35.1™ pump, available commercially from Anschutz, Kiel, Germany.

In an effort to avoid burdening patients with having to undergo an invasive surgical procedure to remove a fixed flow rate pump in order to manually adjust the flow characteristics of the device, drug infusion pumps with flow rates programmable after implantation were developed. These implantable pumps typically are powered by an internal battery. For example, the SynchroMed™ drug infusion pump, available commercially from Medtronic, Inc., Minneapolis, Minn., is an internally powered programmable pump having features which allow physicians to change fluid delivery parameters, such as flow rate, infusion period, ramp time, and bolus volume.

But while internally powered, variable flow rate programmable pumps represent a clear advance over prior fixed flow rate pumps, and they continue to enjoy widespread support and use by physicians worldwide, use of such pumps has drawbacks. For example, the device's useful life is restricted by the life of its internal power supply. An internal power supply eventually becomes depleted; thus, when the pump's internal battery runs out, the patient must undergo a surgical procedure to have the device removed and replaced. Currently, the average useful life of such a device is approximately 4–7 years. Further, in order to guard against the shortening of the device's useful life, such devices typically are not manufactured with additional power-consuming features within the device such as sensors or other medical diagnostic equipment which would prove useful to physicians in treating and monitoring their patients. Such equipment is excluded primarily because of a desire to avoid additional power drain to a device with an implanted power source having a fixed life. Finally, because these pumps are implanted into patients' bodies, it is desirable that they be as small as possible for patient comfort. However, there are limitations on how small the internally powered variable flow rate programmable pump can be made because the internal power source takes up considerable space in the interior of the device.

SUMMARY OF THE INVENTION

As explained in more detail below, the implantable non-invasive rate adjustable pump of the present invention overcomes the above-noted and other shortcomings of prior implantable pumps. In accordance with the present invention, an implantable pump is programmed non-invasively by means of a programmer that communicates flow rate information by means of radio frequency telemetry or other methods of non-invasive telemetry. The programmer also supplies power to the implantable pump during programming. The implanted rate-adjustable pump that receives rate information and power by telemetry preferably does not include a battery or any other type of internal power supply, relying only on the energy obtained from the programmer through telemetry.

The implanted telemetry rate-adjustable pump is "powered up" during programming. To power up the device, the telemetry head of a programmer is placed over the patient's skin in the area in which the pump had been implanted. A telemetry signal then is received by an antenna in the pump, and associated circuitry in the pump is powered up. In other words, the programmer telemetry head sends a signal through the patient's skin in the area in which the pump is implanted. A generally flat coil of wire or other suitable receiving station inside the implanted unit proximate the patient's skin receives the signal, and a voltage is formed in the coil. This voltage, which in general remains as long as the programmer head and signal are in place, serves as a power source for the pump, thus eliminating the need for an internal battery.

Powering up a device using telemetry signals is not uncommon in certain medical applications unrelated to drug infusion pumps, e.g., implantable pulse generators and the like. With those devices, as with drug infusion pumps, there is a desire to make the devices as small as possible for patient comfort. Thus, with certain model stimulators, like the Xtrel™ and Mattrix™ implantable stimulators, commercially available from Medtronic, Inc., Minneapolis, Minn., use of internal batteries has been avoided in favor of an external transmitting unit to power the devices. However, because stimulators require continuous power during operation, patients typically must carry an external transmitting unit with them at all times, usually on their belt.

In the implantable non-invasive rate-adjustable pump of the present invention application, however, the same need for continuous power does not exist. The primary power requirements comprise the energy needed to change the state of a valve or valve network in adjusting flow rates, and to operate certain other medical diagnostic components, e.g., sensors.

In accordance with the present invention, to change the flow rate of a drug infusion pump, the programmer sends, at the user's direction, flow rate programming commands or other signals using telemetry to the pump circuitry. In changing the flow rate, for example, signals sent to the pump circuitry would change the operating parameters of the electromechanical system that regulates the flow rate. Once the system is set in place, the system would not change its flow rate setting unless reprogrammed by the programmer. After all commands are sent and the desired programming and reprogramming of systems is complete, the programmer is taken away from the patient's skin. The pump then "powers down" and assumes a discharged state, keeping the newly programmed fluid flow rate settings.

In accordance with the present invention, then, in an adjustable rate implantable pump that is not limited by the life of a battery, options exist for flow rate adjustment methods and apparatus that would not be used in a pump whose life is limited by the life of the battery. For example, in a non-invasively powered adjustable rate implantable pump in which power is needed only to change flow rates, and a pressurized reservoir maintains a fixed rate of flow through a restrictor network, the network preferably comprises a reservoir attached to a manifold with n bi-stable valves or a multi-stable valve with m states. These valves could be of various design, including, for example, shape-memory valves and bimetallic or laminated silicon/metal micromachined valves. The valves control the flow to n restrictors or regulators or a single restrictor or regulator when used with a multi-stable valve. With the bi-stable valve configuration, each restrictor has a different target flow rate, and the combination overall allows for $2^n$ flow rate options. With the multi-stable valves, the system has m flow rates. Both types of valves have no requirement for power except during flow rate changes. That power is provided by telemetry.

Thus, a non-invasively rate-adjustable pump in accordance with the present invention has an advantage over prior single rate restrictor pumps in that a new target rate can be selected non-invasively after the pump has been implanted by changing the state of a valve or valves. Further, the pump has advantages over prior implantable programmable pumps in that it can be used without an internal power supply that can run down and need to be replaced. Also, because a battery or other internal power supply is not required, the device can be built smaller in size. Finally, the power from the telemetry head may also be used to power electrical components in the pump, e.g., additional power-consuming components such as sensors for measuring flow rates; sensors for measuring drug volume in the reservoir; a needle detector for the septum; and any of the other additional useful components requiring energy in order to function.

DETAILED DESCRIPTION OF THE INVENTION

Figure 1:
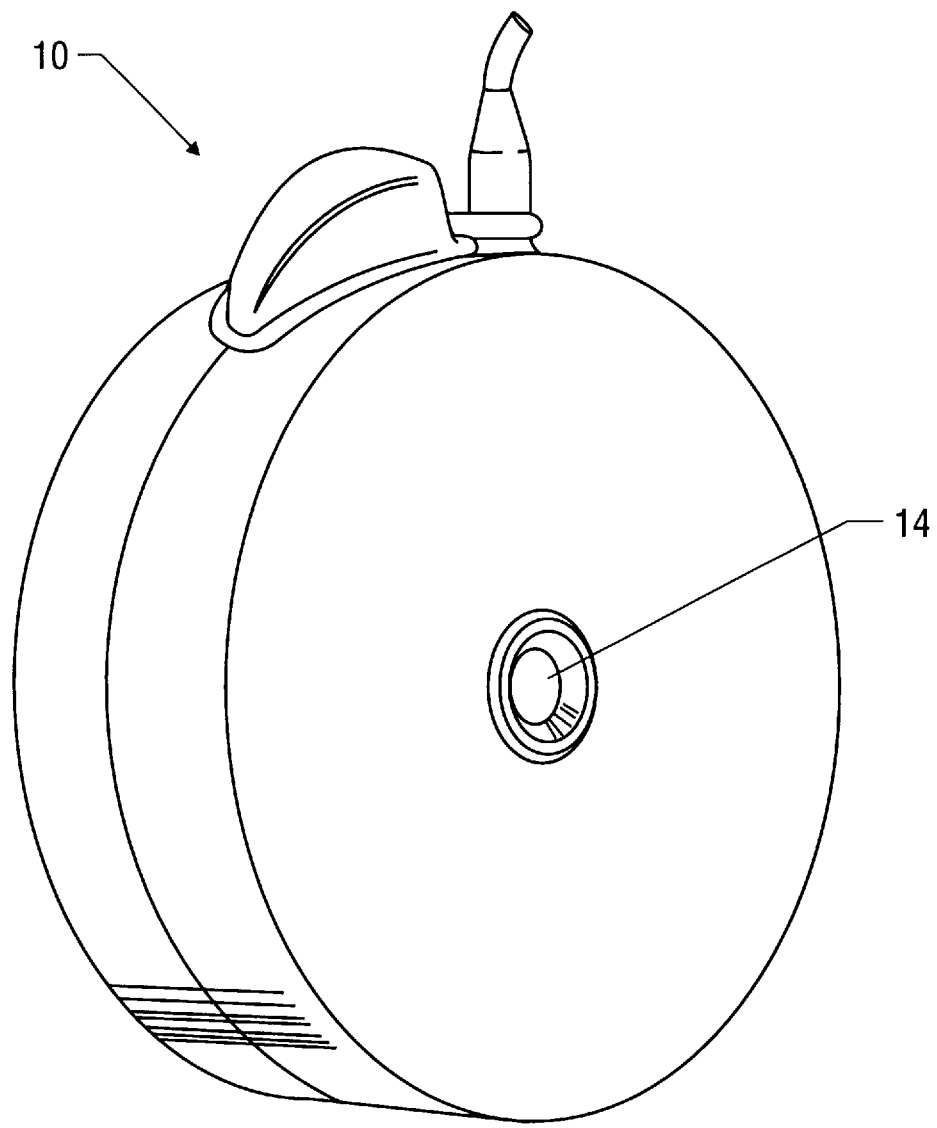
FIG. 1 is a schematic illustration of an exemplary implantable drug infusion pump in accordance with the present invention.
Figure 2:
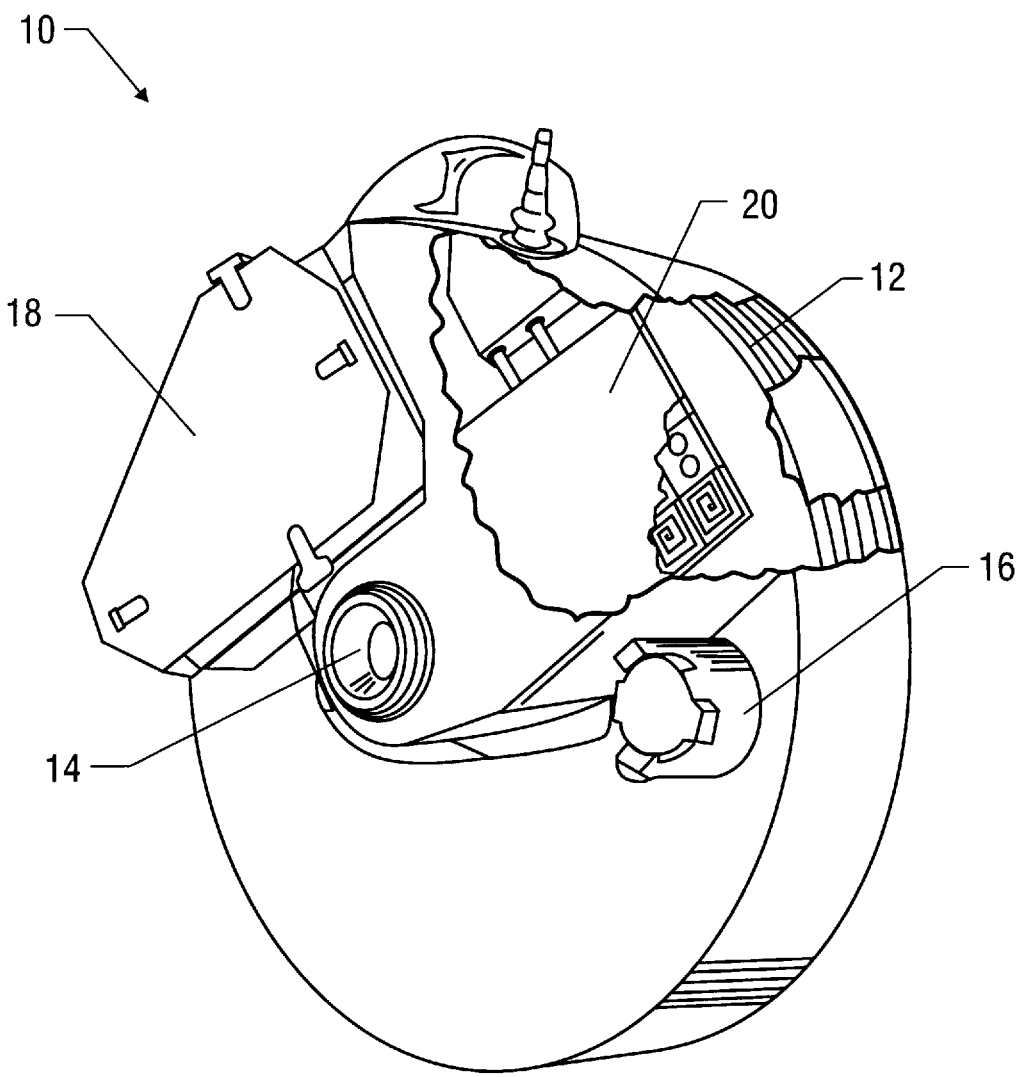
FIG. 2 is a schematic cut-away illustration of the exemplary implantable drug infusion pump of the present invention shown in FIG. 1, but with the top portion removed.

In accordance with the present invention, as shown in FIGS. 1–2, a drug infusion pump 10 includes a fluid reservoir 12 and a septum 14 which serves, for example, as an access port to the reservoir 12 during the filling of the reservoir with pharmaceutical agents or other fluids to be delivered to a specific desired location within a patient's body. The pump 10 further includes a telemetry antenna or receiver 16 preferably comprising a coil of wire within which a voltage may be induced when the receiver 16 is in the presence of a transmitted signal. Such a signal is created, for example, by an assembly including a programmer operatively coupled to a radio frequency head disposed proximate to a pump 10 implanted within the body of a patient near the skin.

The pump 10 further includes a system 20 that regulates the flow of fluid from the reservoir 12. Preferably, the system 20 comprises a valve network assembly adjustable to a plurality of flow rate settings, and includes a plurality of bi-stable valves that control the flow of fluid to a plurality of flow restrictors. The valves are similar to, but not restricted to those described by Wagner, et al. See. Wagner, B. et al., "Bistable Microvalve with Pneumatically Coupled Membranes," IEEE 0-7803-2985-6/96, pp. 384–88, which is incorporated herein by reference. The restrictors are similar to, but not limited to capillary tube technology used in the commercially available Infusaid and Anschütz fixed rate pumps. Alternatively, micro-machined etching technology can also be used to manufacture the restrictor.

In addition, the pump 10 preferably includes control circuitry 18 for changing the state of one or more of the valves of the system 20 in response to a received telemetry signal. The control circuitry 18 preferably includes elements required to communicate with the transmitter, transform the signal from the transmitter to energy required to change valve states according to the telemetry received via the transmitter, and verify valve states and overall pump performance.

Figure 3:
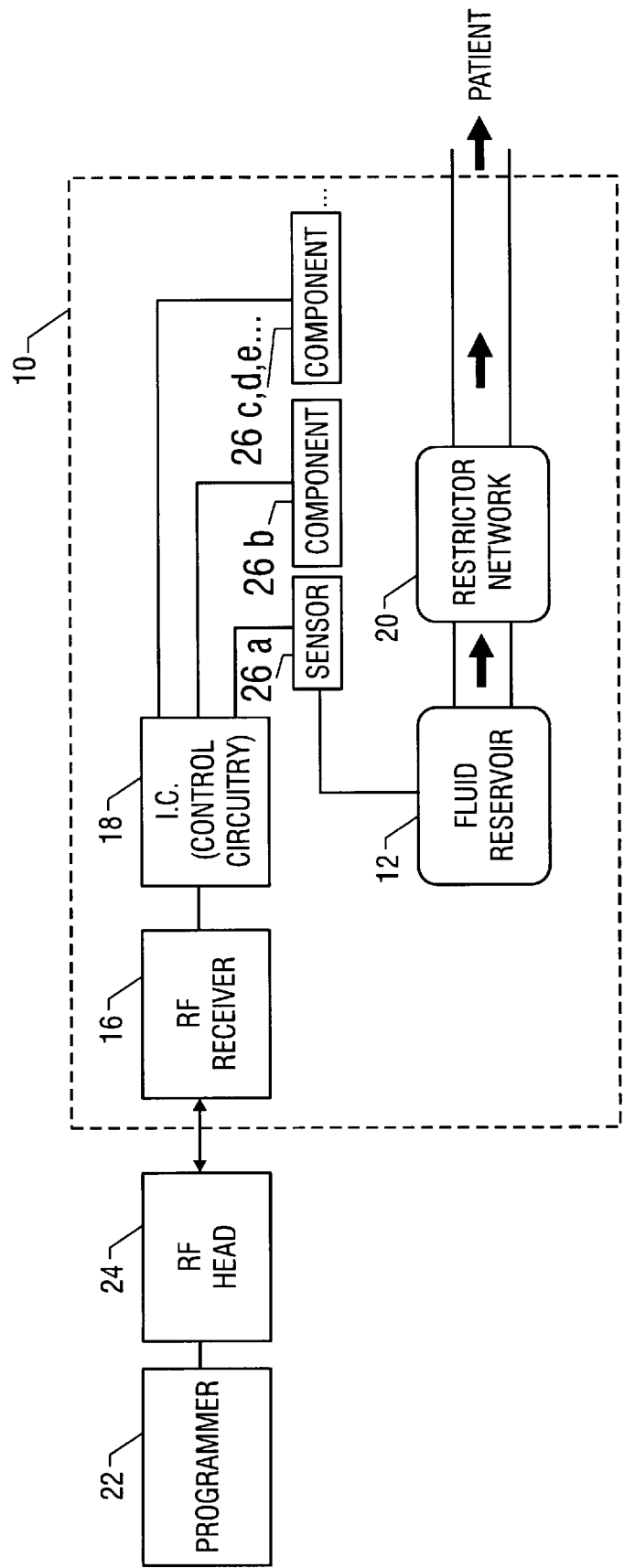
FIG. 3 is a schematic illustration in block diagram form of an implantable non-invasive rate-adjustable pump system in accordance with the present invention.

FIG. 3 shows a schematic illustration of an implantable non-invasive rate-adjustable pump system in accordance with the present invention. As shown therein, the pump 10 preferably also includes a plurality of sensors and other components 26 (a, b, c, . . . ) for use by physicians as diagnostic tools as part of the overall medical treatment plan for the patient. For example, as shown in FIG. 3, sensor 26(a) comprises a tool for measuring drug volume in the reservoir 12; and component 26(b) comprises a sensor for measuring flow rates. The components 26 (a, b, c, . . . ) generally are power-consuming components which, referably receive their energy from non-invasive programming signals or sense commands originating in a programmer or some other similar device.

Although the preferred embodiment of this invention has been described hereinabove in some detail, it should be appreciated that a variety of embodiments will be readily available to persons utilizing the invention for a specific end use. The description of the apparatus and method of this invention is not intended to be limiting on this invention, but is merely illustrative of the preferred embodiment of this invention. Other apparatus and methods which incorporate modifications or changes to that which has been described herein are equally included within this application. Additional objects, features and advantages of the present invention will become apparent by referring to the above description of the invention in connection with the accompanying drawings.

What is claimed is:

1. An implantable medical pump, comprising:
   a fluid reservoir;
   a passive regulator assembly adjustable to a plurality of flow rate settings for regulating the flow of fluid from the fluid reservoir;
   electromechanical control means for changing the passive regulator assembly from a first flow rate setting to a second flow rate setting when the electromechanical control means receives an induced voltage and in response to control signals; and means for receiving radio frequency signals operative to maintain the induced voltage in the electromechanical control means in response to received radio frequency signals.

2. The implantable medical pump of claim 1, wherein the means for receiving radio frequency signals is further operative to provide control signals to the electromechanical control means in response to received radio frequency signals.

3. The implantable medical pump of claim 2, wherein the regulator assembly for regulating the flow of fluid from the fluid reservoir comprises a valve.

4. The implantable medical pump of claim 2, wherein the regulator assembly for regulating the flow of fluid from the fluid reservoir comprises a valve and a flow restrictor, and wherein the valve is operatively coupled to the flow restrictor.

5. The implantable medical pump of claim 2, wherein the regulator assembly for regulating the flow of fluid from the fluid reservoir comprises a plurality of valves and a flow restrictor network which are operatively coupled.

6. The implantable medical pump of claim 2, wherein the radio frequency signals are received from a programmer.

7. The implantable medical pump of claim 2, further comprising means for sensing, in response to a received radio frequency sense command, the amount of fluid in the fluid reservoir.

8. The implantable medical pump of claim 7, wherein the sense command is received from a programmer.

* * * * *